United States Patent
Rhynes

[11] Patent Number: 5,880,779
[45] Date of Patent: Mar. 9, 1999

[54] STERILE DISPOSABLE WHITE BALANCE BOX

[76] Inventor: Vincent Rhynes, 9715 E. Park St., Apartment A, Bellflower, Calif. 90706

[21] Appl. No.: 871,695

[22] Filed: Jun. 9, 1997

[51] Int. Cl.⁶ .................................................. H04N 9/73
[52] U.S. Cl. ..................... 348/223; 348/655; 348/376; 348/241
[58] Field of Search ...................... 348/223, 187, 348/65, 373, 376, 655, 241, 248; 422/1, 34, 104; 312/1

[56] References Cited

U.S. PATENT DOCUMENTS

| | | | |
|---|---|---|---|
| 5,305,098 | 4/1994 | Matsunaka et al. | 348/65 |
| 5,365,267 | 11/1994 | Edwards | 348/65 |
| 5,498,230 | 3/1996 | Adair | 600/112 |
| 5,702,669 | 12/1997 | Green | 422/30 |

*Primary Examiner*—Andrew I. Faile
*Assistant Examiner*—Habte Bahgi

[57] ABSTRACT

A sterile disposable white balance box including a housing of a pure white color having a bore formed therein. Also included is a penetrable seal formed about the bore of the housing whereby the seal is adapted to be penetrated by a scope rod whereupon a seal is afforded about a periphery of the scope rod.

7 Claims, 2 Drawing Sheets

STERILE DISPOSABLE WHITE BALANCE BOX

BACKGROUND OF THE INVENTION

1. Field of the Invention

The present invention relates to a sterile disposable white balance box and more particularly pertains to allowing proper camera white setting of a surgical rod lens telescope.

2. Description of the Prior Art

The use of white balancing targets is known in the prior art. More specifically, white balancing targets heretofore devised and utilized for the purpose of camera white setting are known to consist basically of familiar, expected and obvious structural configurations, notwithstanding the myriad of designs encompassed by the crowded prior art which have been developed for the fulfillment of countless objectives and requirements.

By way of example, the prior art includes U.S. Pat. No. 4,527,189 to Ooi et al.; U.S. Pat. No. 5,365,267 to Edwards; U.S. Pat. No. 5,099,316 to Ogawa; U.S. Pat. No. 4,739,394 to Oda et al.; U.S. Pat. No. 5,389,969 to Suzuki et al.; and U.S. Pat. No. 5,155,635 to Kakiuchi.

In this respect, the sterile disposable white balance box according to the present invention substantially departs from the conventional concepts and designs of the prior art, and in so doing provides an apparatus primarily developed for the purpose of allowing proper camera white setting of a surgical rod lens telescope.

Therefore, it can be appreciated that there exists a continuing need for a new and improved sterile disposable white balance box which can be used for allowing proper camera white setting of a surgical rod lens telescope. In this regard, the present invention substantially fulfills this need.

SUMMARY OF THE INVENTION

In view of the foregoing disadvantages inherent in the known types of white balancing targets now present in the prior art, the present invention provides an improved sterile disposable white balance box. As such, the general purpose of the present invention, which will be described subsequently in greater detail, is to provide a new and improved sterile disposable white balance box which has all the advantages of the prior art and none of the disadvantages.

To attain this, the present invention essentially comprises a housing having a hollow rectilinear configuration with a closed rectangular front face, a closed rectangular rear face, a pair of closed rectangular side faces, a closed square bottom face, and a square top face. Preferably, the housing has a height of approximately 3 inches and a length of approximately 1 and ¾ inches. As shown in FIGS. 3 & 4, the housing has an outer layer constructed from a rigid plastic. The outer layer has a circular bore formed in the top face of the housing. Such bore has a first diameter which is preferably 19 mm. The outer layer further has a circular inset portion formed in an outer surface of the top face of the housing in coaxial relationship with the circular bore. The circular inset portion ideally has a second diameter greater than the first diameter. The housing further has an inner layer constructed from a styrofoam of a pure white color. The inner layer has a circular bore formed in a top face of the housing in coaxial relationship with the circular bore of the outer layer. As can be seen in FIG. 3, the circular bore of the inner layer has a diameter which is the same as that of the outer layer. Also included is a thin plastic seal having a circular shape with the second diameter. The seal is coupled to an upper surface of the inset portion of the outer layer of the housing. It is imperative that the thin plastic seal be adapted to preclude light penetration and further be of a pure white color. By this structure, the seal is adapted to be penetrated by a scope rod whereupon a seal is afforded about a periphery of the scope rod.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sterile disposable white balance box which has all the advantages of the prior art white balancing targets and none of the disadvantages.

It is another object of the present invention to provide a new and improved sterile disposable white balance box which may be easily and efficiently manufactured and marketed.

It is a further object of the present invention to provide a new and improved sterile disposable white balance box which is of a durable and reliable construction.

An even further object of the present invention is to provide a new and improved sterile disposable white balance box which is susceptible of a low cost of manufacture with regard to both materials and labor, and which accordingly is then susceptible of low prices of sale to the consuming public, thereby making such sterile disposable white balance box economically available to the buying public.

Still yet another object of the present invention is to provide a new and improved sterile disposable white balance box which provides in the apparatuses and methods of the prior art some of the advantages thereof, while simultaneously overcoming some of the disadvantages normally associated therewith.

Still another object of the present invention is to allow proper camera white setting of a surgical rod lens telescope.

Lastly, it is an object of the present invention to provide a new and improved sterile disposable white balance box including a housing of a pure white color having a bore formed therein. Also included is a penetrable seal formed about the bore of the housing whereby the seal is adapted to be penetrated by a scope rod whereupon a seal is afforded about a periphery of the scope rod.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference characters refer to similar parts throughout the several views of the drawings.

DESCRIPTION OF THE PREFERRED EMBODIMENT

Figure 1:
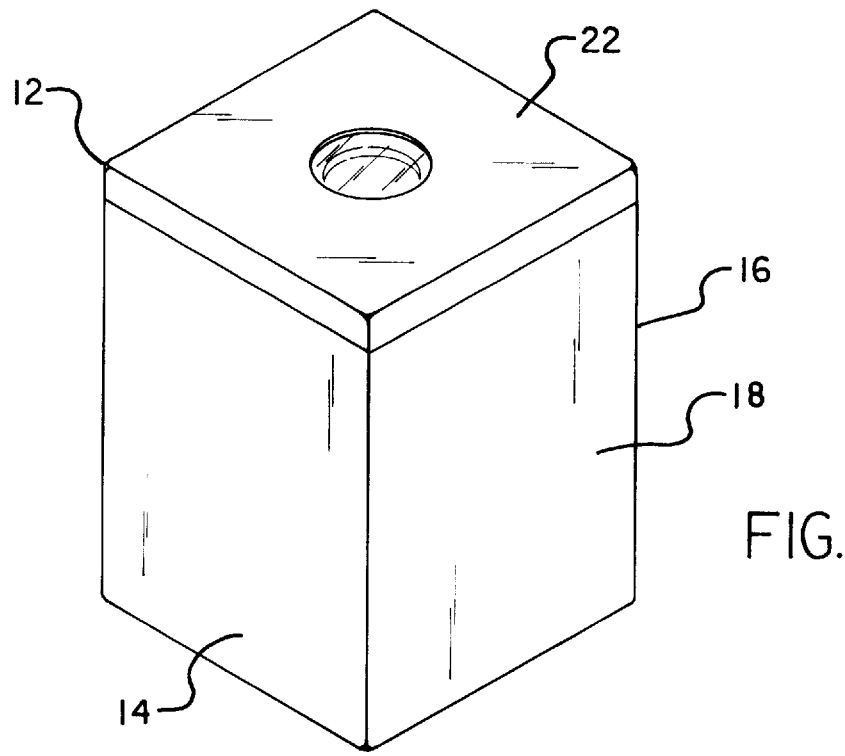
FIG. 1 is a perspective illustration of the preferred embodiment of the sterile disposable white balance box constructed in accordance with the principles of the present invention.
Figure 2:
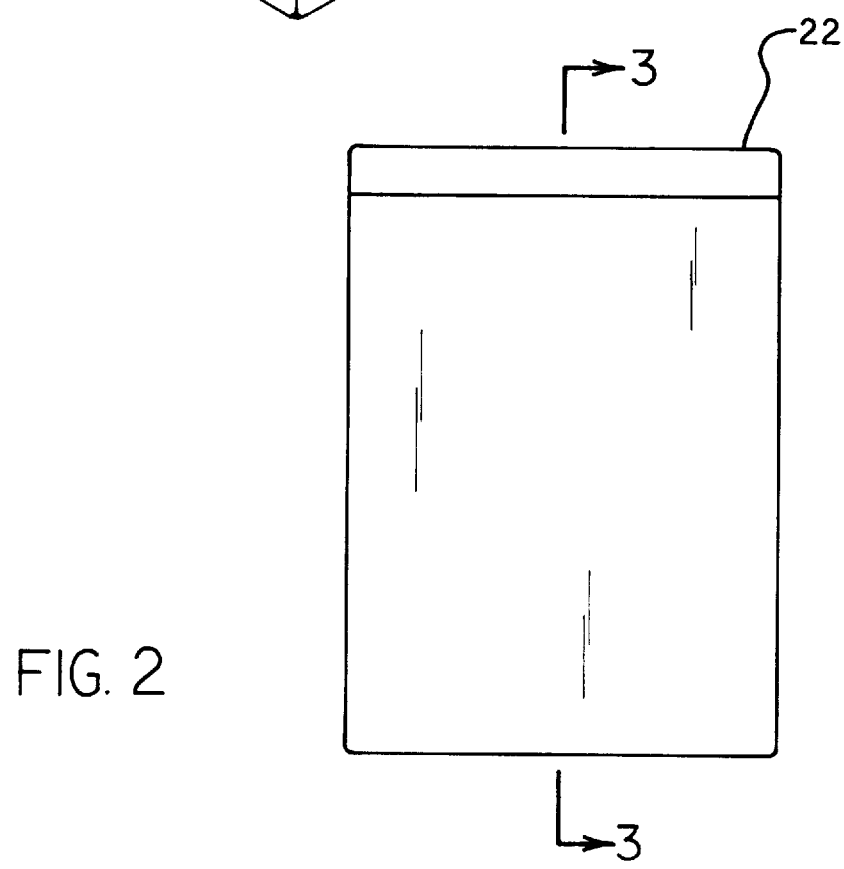
FIG. 2 is a side view of the housing of the present invention.

With reference now to the drawings, and in particular to FIG. 1 thereof, a new and improved sterile disposable white balance box embodying the principles and concepts of the present invention and generally designated by the reference numeral 10 will be described.

The present invention, the new and improved sterile disposable white balance box, is comprised of a plurality of components. Such components in their broadest context include housing with an inner and outer layer and a seal. Such components are individually configured and correlated with respect to each other so as to attain the desired objective.

Figure 3:
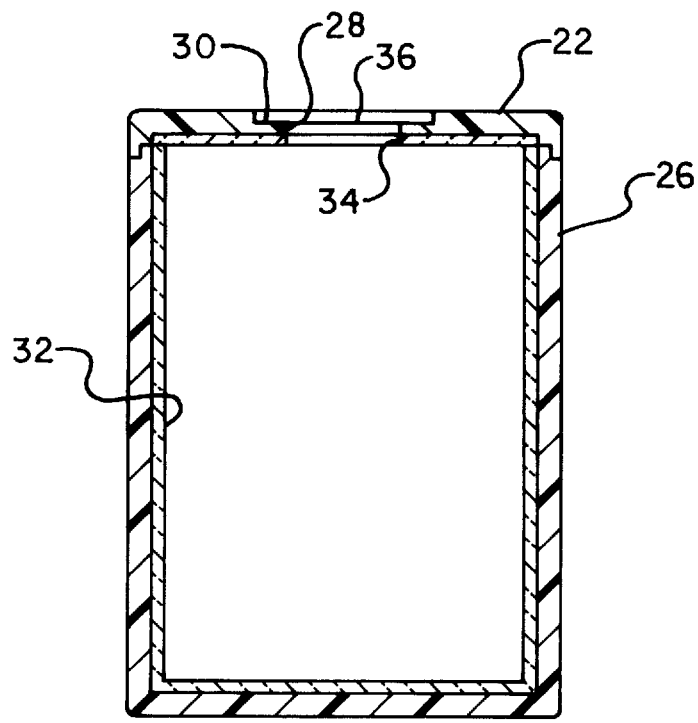
FIG. 3 is a cross-sectional view of the housing taken along line 3—3 shown in FIG. 2.
Figure 4:
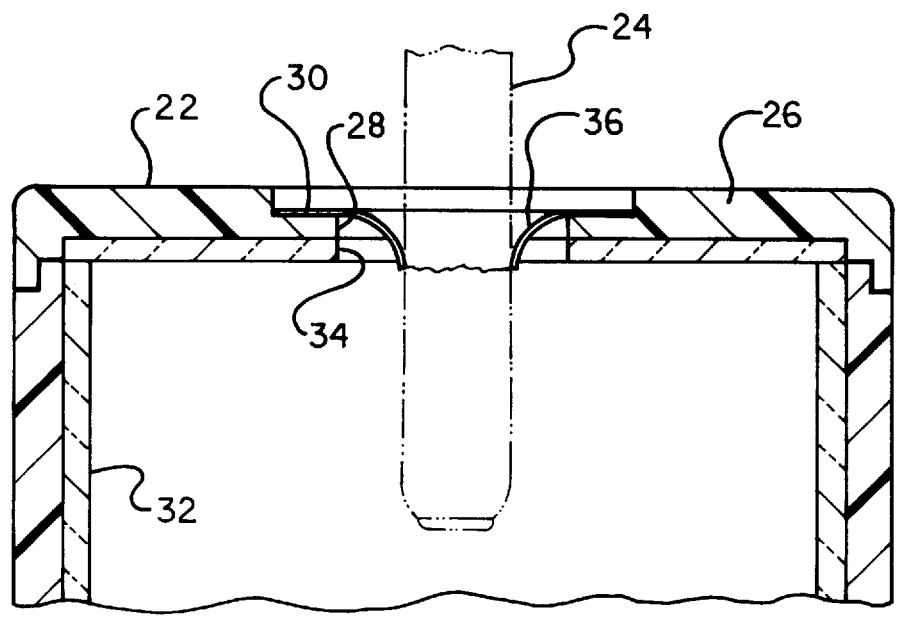
FIG. 4 is a close-up of the housing shown in FIG. 3.

More specifically, it will be noted that the system 10 of the present invention includes a housing 12 having a hollow rectilinear configuration with a closed rectangular front face 14, a closed rectangular rear face 16, a pair of closed rectangular side faces 18, a closed square bottom face 20, and a square top face 22. All of such faces are planar and integrally coupled or in the alternative, glued together. Preferably, the housing has a height of approximately 3 inches and a length and width of approximately 1 and ¾ inches. As will become apparent later, such height, width and length are critical for providing adequate and proper room when a rod lens telescope 24 is inserted therein. As shown in FIGS. 3 & 4, the housing has an outer layer 26 constructed from a rigid plastic. The outer layer has a circular bore 28 formed in a central extent of the top face of the housing. Such bore has a first diameter which is preferably 19 mm. The outer layer further has a circular inset portion 30 formed in an outer surface of the top face of the housing in coaxial relationship with the circular bore. The circular inset portion ideally has a second diameter greater than the first diameter.

The housing further has an inner layer 32 constructed from a styrofoam of a pure white color. Ideally, the inner layer has a thickness of at least 1/16 of an inch. The inner layer has a circular bore 34 formed in a top face of the housing in coaxial relationship with the circular bore of the outer layer. As can be seen in FIG. 3, the circular bore of the inner layer has a diameter which is the same as that of the outer layer.

Also included is a thin plastic seal 36 having a circular shape with the second diameter. The seal is coupled to an upper surface of the inset portion of the outer layer of the housing. Such coupling is ideally accomplished with an adhesive. The diameter of the circular inset portion is preferably large enough to afford an adequate surface to which the seal is adhered. It is imperative that the thin plastic seal be adapted to preclude light penetration and further be of a pure white color. In the preferred embodiment, the material and thickness of the seal closely resemble cellophane wrap often utilized in the food industry. The only difference, of course, is that the seal is light impermeable. By this structure, the seal is adapted to be easily penetrated by a scope rod whereupon a seal is afforded about a periphery of the scope rod.

In use, the present invention may be used to provide an ideal environment for white balancing a surgical camera system. As such, adequate "white coverage" is afforded in front of the rod lens so that camera white setting may be properly preformed. It is imperative that at least the interior space of the box be subject to a sterilization process which utilizes Ethylene Oxide Gas(E.T.O.). It should be further noted that due to the "BIO-BURDON" release from Ethylene Oxide Gas residue, the present invention may be disposed in a convenient and safe manner.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved sterile disposable white balance box comprising, in combination:

a housing having a hollow rectilinear configuration with a closed rectangular front face, a closed rectangular rear face, a pair of closed rectangular side faces, a closed square bottom face, and a square top face, the housing having an outer layer constructed from a rigid plastic, the outer layer having a circular bore formed in the top face of the housing with the bore having a first diameter, the outer layer further having a circular inset portion formed in an outer surface of the top face of the housing in coaxial relationship with the circular bore and having a second diameter greater than the first diameter, the housing further having an inner layer constructed from a styrofoam of a pure white color, the inner layer having a circular bore formed in a top face of the housing in coaxial relationship with the circular bore of the outer layer, the circular bore of the inner layer having the first diameter; and a thin plastic seal having a circular shape with the second diameter, the seal coupled to an upper surface of the inset portion of the outer layer of the housing, the thin plastic seal adapted to preclude light penetration, whereby the seal is adapted to be penetrated by a scope rod whereupon a seal is afforded about a periphery of the scope rod;

said housing having a height of approximately 3 inches;

said first diameter being approximately 19 mm.

2. A sterile disposable white balance box comprising:

a housing of a pure white color having a bore formed therein, the housing having a hollow rectilinear configuration with a closed rectangular front face, a closed rectangular rear face, a pair of closed rectangular side faces, a closed square bottom face, and a square top face, the housing having an outer layer constructed from a rigid plastic, the outer layer having a circular bore formed in the top face of the housing with the bore having a first diameter, the outer layer further having a circular inset portion formed in an outer surface of the top face of the housing in coaxial relationship with the circular bore and having a second diameter greater than the first diameter, the housing further having an inner layer constructed from a styrofoam of a pure white color; and penetrable seal means positioned about the bore of the housing whereby the seal is adapted to be penetrated by a scope rod whereupon a seal is afforded about a periphery of the scope rod.

3. A sterile disposable white balance box as set forth in claim 2 wherein the housing is constructed from styrofoam.

4. A sterile disposable white balance box as set forth in claim 2 wherein the housing has a height of approximately 3 inches.

5. A sterile disposable white balance box as set forth in claim 2 wherein the bore has a diameter of approximately 19 mm.

6. A sterile disposable white balance box as set forth in claim 2 wherein at least an interior of the box is sterile utilizing Ethylene Oxide Gas.

7. A sterile disposable white balance box as set forth in claim 6 wherein the box is safely disposable.

\* \* \* \* \*